(12) United States Patent
Meffin et al.

(10) Patent No.: US 9,381,341 B2
(45) Date of Patent: Jul. 5, 2016

(54) ELECTRICALLY CONDUCTIVE IMPLANTABLE MEDICAL DEVICE

(71) Applicants: The University of Melbourne, Melbourne, Victoria (AU); National ICT Australia Limited, Eveleigh, New South Wales (AU)

(72) Inventors: Hamish Meffin, Eveleigh (AU); Kate Fox, Melbourne (AU); David Garrett, Eveleigh (AU); Kumaravelu Ganesan, Melbourne (AU); Steven Prawer, Melbourne (AU); Samantha Lichter, Melbourne (AU); Igor Aharonovich, Melbourne (AU)

(73) Assignees: The University of Melbourne, Parkville (AU); National ICT Australia Limited, Eveleigh (AU)

( * ) Notice: Subject to any disclaimer, the term of this patent is extended or adjusted under 35 U.S.C. 154(b) by 111 days.

(21) Appl. No.: 14/095,459

(22) Filed: Dec. 3, 2013

(65) Prior Publication Data
US 2014/0094885 A1  Apr. 3, 2014

Related U.S. Application Data

(63) Continuation of application No. PCT/AU2012/000609, filed on May 31, 2012.

(60) Provisional application No. 61/561,533, filed on Nov. 18, 2011.

(30) Foreign Application Priority Data

Jun. 3, 2011 (AU) .............................. 2011902190
Nov. 18, 2011 (AU) .............................. 2011904827

(51) Int. Cl.
*A61N 1/05* (2006.01)
*A61N 1/375* (2006.01)

(52) U.S. Cl.
CPC ............... *A61N 1/05* (2013.01); *A61N 1/0543* (2013.01); *A61N 1/3754* (2013.01); *A61N 1/0529* (2013.01); *A61N 1/0551* (2013.01); *Y10T 29/49165* (2015.01); *Y10T 29/49204* (2015.01)

(58) Field of Classification Search
CPC ... A61N 1/375; A61N 1/3752; A61N 1/3754; A61N 1/05; A61N 1/0543; H01L 23/481; Y10T 29/49204
USPC .................................................... 607/36, 116
See application file for complete search history.

(56) References Cited

U.S. PATENT DOCUMENTS 5,844,252 A * 12/1998 Shiomi ................. H01J 1/3042
257/10
6,812,404 B1   11/2004 Martinez (Continued)

FOREIGN PATENT DOCUMENTS

EP        1947220 A4    8/2009
WO   WO2004071338 A2   8/2004

(Continued)

OTHER PUBLICATIONS

International Search Report for International Application No. PCT/AU2012/000609, mailed Aug. 28, 2012.

(Continued)

*Primary Examiner* — Christopher D Koharski
*Assistant Examiner* — Michael Carey
(74) *Attorney, Agent, or Firm* — Fish & Richardson P.C.

(57) ABSTRACT

The present disclosure provides an electrode and an feedthrough for an implantable medical device. In one embodiment, the implantable electrode and the implantable feedthrough both comprise electrically insulating diamond material and electrically conductive diamond material that form an interface. Further, the present disclosure provides method for fabricating the implantable electrode and the feedthrough.

20 Claims, 15 Drawing Sheets

(56) References Cited

U.S. PATENT DOCUMENTS

| | | |
|---|---|---|
| 7,565,203 B2 | 7/2009 | Greenberg |
| 8,177,949 B2 | 5/2012 | Pickles et al. |
| 8,491,765 B2 | 7/2013 | Pickles et al. |
| 2002/0120296 A1 | 8/2002 | Mech |
| 2005/0092507 A1 | 5/2005 | Marshall |
| 2006/0175953 A1 | 8/2006 | Swain |
| 2010/0084634 A1* | 4/2010 | Gamo et al. ............ 257/40 |
| 2011/0106205 A1* | 5/2011 | Reiterer et al. ......... 607/37 |

FOREIGN PATENT DOCUMENTS

| | | |
|---|---|---|
| WO | WO2011053539 A1 | 5/2011 |
| WO | WO2011154455 A1 | 12/2011 |

OTHER PUBLICATIONS

Ganesan, K., et al., Diamond Penetrating Electrode Array for Epi-Retinal Prothesis, Conf Proc IEEE Eng.Med. Bio. Sci. 2010, pp. 6757-6760.

* cited by examiner

Figure 12,(b)

ELECTRICALLY CONDUCTIVE IMPLANTABLE MEDICAL DEVICE

FIELD OF THE INVENTION

The present invention relates to an electrode and a feedthrough and relates particularly, though not exclusively, to an implantable medical device, such as a retinal prosthesis.

BACKGROUND OF THE INVENTION

Medical devices that include electronic components are frequently implanted into the human body. Such medical devices include cochlear implants, pacemakers, retinal prostheses and other devices. It is important that the electronic components of such medical devices are protected from fluid exposure. Further, it is of critical importance for the health of a patient that an exterior of the devices is formed from a biocompatible material and exposure of non-biocompatible materials to tissue and body fluids is avoided.

Electronic components used in such medical devices usually contain a range of materials. One material that is often used is silicon, which unfortunately is not biocompatible and consequently biocompatible coatings or encasings are required. One frequent failure of such medical devices is caused by breaking of interfaces between the different materials. Surface coatings can degrade over time, which can have fatal consequences. Further, polymeric or glass materials are often used to seal apertures of electrical feedthroughs and degrading of these materials over time can also have fatal consequences.

SUMMARY OF THE INVENTION

The present invention provides in a first aspect an electrode for an implantable medical device, the electrode comprising:
  a plurality of electrically conductive elements comprising a diamond material, the diamond material being a nitrogen incorporated diamond material; and
  at least one electrically insulating element covering at least a portion of each electrically conductive element and comprising a diamond material.

Throughout this specification the term "diamond material" is used for films or bulk materials of crystalline diamond material, poly-crystalline diamond material, nano-crystalline diamond material and also for diamond-like materials including diamond glassy carbon and diamond-like carbon materials.

Each electrically conductive element typically has a first end and a second end that is opposite the first end. Each electrically conductive element may be positioned such that the first and second ends of the electrically conductive material are exposed prior to contacting with another medium. One of the first and second ends of each electrically conductive element typically is arranged to establish contact with an electrical component or conductor and the other end typically is arranged to establish contact with a biological medium. The electrode may exclusively be formed a diamond material. Alternatively, the electrode may exclusively comprise a diamond material and a metallic material. The electrode material typically is free from silicon or another semiconducting material.

Embodiments of the present invention have significant advantages. Diamond is a biocompatible and strong material that is impermeable to fluid ingress. The use of a single type of material for the electrically conductive and the electrically insulating elements results in a particularly strong interface between the at least one electrically conductive element and the insulating element.

At least one of the diamond materials may comprise a dopant or incorporated material that influences an electrical property of the material. For example, the diamond material of the at least one electrically conductive element may be nitrogen or boron incorporated or doped.

In one embodiment, the electrode is arranged for use as a stimulating electrode for stimulating biological tissue such as nerve tissue.

Each electrically conductive element typically is in direct contact with the at least one electrically insulating element and an interface between the electrically conductive elements and at least one electrically insulating element typically is hermetically sealed.

The diamond material of the at least one electrically conductive element may for example be a nano-crystalline diamond material, such as a nitrogen incorporated or doped nano-crystalline diamond material.

The diamond materials of the at least one electrically conductive element and/or the diamond material of the electrically insulating element may be formed using a suitable thin film growth technique, such as chemical vapour deposition.

The electrically conductive elements may be arranged in an array.

The present invention provides in a second aspect an electrode for an implantable medical device, the electrode comprising:
  a plurality of electrically conductive elements formed from a first material that comprises an electrically conductive nitrogen incorporated diamond material; and
  at least one electrically insulating element formed from a second material and covering at least a portion of each electrically conductive element;
  wherein the first and second materials have substantially the same crystallographic structures and lattice constants.

The present invention provides in a third aspect a medical device comprising the electrode in accordance with the first or second aspect of the present invention, the medical device comprising:
  a housing portion that defines an interior region; and
  electronic components positioned in the interior region of the housing portion.

In one example, the electrode comprises an array of the electrically conductive elements and forms a lid of the housing portion. Walls of the housing portion typically are formed from a diamond material and may further comprise a feedthrough for connecting the electronic components positioned in the interior of the housing portion with further components positioned at a remote location. The medical device typically is arranged such that the interior region is hermetically sealed and has an outer surface that is formed from a biocompatible material.

The present invention provides in a fourth aspect a method of manufacturing an electrode for an implantable medical device, the method comprising the steps of:
  forming a plurality of electrically conductive elements comprising a diamond material, the diamond material being a nitrogen incorporated diamond material;
  forming a least one electrically insulating element that covers at least portions of the electrically conductive elements and comprises a diamond material in a manner such that the diamond material of the electrically conductive elements and the diamond material of the at least one electrically insulating element are in direct contact and an interface between the first and second materials is hermetically sealed.

The present invention provides in a fifth aspect a method of manufacturing an electrode for an implantable medical device, the method comprising the steps of:
- forming a plurality of electrically conductive elements comprising an electrically conductive nitrogen incorporated diamond material;
- forming a least one electrically insulating element that covers at least portions of the electrically conductive elements and comprises a second material in a manner such that the electrically conductive nitrogen incorporated diamond material and the second material are in direct contact and an interface between the materials is hermetically sealed;
- wherein the materials have substantially the same crystallographic structure and lattice constant.

In the fourth and fifth aspects of the present invention the first and second materials typically are both diamond materials. The method in accordance with either aspect of the present invention typically comprises forming at least at portion of the diamond material on a substrate, such as a silicon substrate, and removing at least a portion of the substrate, typically the entire substrate, after formation of the diamond material. The electrically conductive elements typically are formed such that the electrically conductive elements have exposed opposite ends prior to contacting with another medium. Further, forming the first and second materials typically comprise depositing the diamond material using chemical vapour deposition (CVD), which may further comprise etching at least a portion of the formed materials.

The present invention provides in a sixth aspect an implantable medical device having an electrical feedthrough, the device comprising:
a housing portion having an exterior surface and an aperture;
- an electrically conductive material penetrating though the aperture of the housing portion and being arranged for electrically coupling a component positioned inside the housing with a component that is exterior the housing, the electrically conductive material comprising a diamond material, the diamond material being a nitrogen incorporated diamond material; and
- an electrically insulating material positioned over the electrically conductive material to provide electrical insulation, the electrically insulating material comprising a diamond material;
wherein the electrically conductive and the electrically insulating materials are arranged such that the aperture is sealed and the housing is fluid impermeable in the proximity of the feedthrough.

Throughout this specification the term "fluid" is used for liquid or gaseous media.

The aperture typically is sealed around the electrically conductive material using a single material component that may be "anchored" in the aperture and may also coat an area surrounding the aperture, which provides a particularly strong seal.

In one embodiment the electrically insulating material also comprises a diamond material and seals the aperture. For example, the electrically insulating material may be composed of a poly-crystalline diamond material such as hydrogen-incorporated ultra nano-crystalline diamond. The electrically insulating material may comprise a first portion that has penetrated into the aperture and provides a seal between the electrically conductive material and the housing portion and a second portion that coats a portion of the housing portion around the aperture. The first and second portions of the electrically insulating material comprising the diamond material typically are integrally formed and form one part that is rigidly coupled to the housing portion and the electrically conductive material.

The diamond material of the electrically conductive material may be a nitrogen-incorporated diamond material (for example nitrogen-incorporated ultra nano-crystalline diamond). The electrically conductive material may also be electrically coupled to another electrically conductive material portion, such as a metallic wire or the like, that may at least in part penetrate through the aperture and may be composed for example of platinum, gold or another suitable metallic material.

The electrically conductive material may also comprise a portion that coats a portion of the housing portion around the aperture. The electrically conductive material typically is integrally formed and forms one part that is rigidly coupled to the housing portion. The electrically insulating material typically is positioned over the electrically conductive material such that electrical insulation is established.

The present invention provides in a seventh aspect a method of manufacturing a feedthrough for an implantable medical device, the method comprising the steps of:
- providing a wall portion of a housing of the device;
- forming an aperture through the wall portion;
- forming an electrically conductive material such that the electrically conductive material penetrates though the aperture of the housing portion and is arranged for electrically coupling a component positioned inside the housing with a component that is exterior the housing, the electrically conductive material comprising a nitrogen incorporated diamond material; and
- forming an electrically insulating material positioned over the electrically conductive material to provide electrical insulation, the electrically insulating material comprising a diamond material;
- wherein at least one of the electrically conductive and the electrically insulating material is positioned such that the aperture is sealed and the housing is fluid impermeable in the proximity of the feedthrough.

The electrically insulating material may comprise the diamond material and the step of forming the electrically insulating material comprise depositing the electrically insulating material such that at least a portion of the electrically insulating material penetrates into the aperture and seals the aperture and another portion of the electrically insulating material is deposited at a portion around the aperture.

Alternatively or additionally, the electrically conductive material may comprise the diamond material and the step of forming the electrically conductive material comprises depositing the electrically conductive material such that at least a portion of the electrically conductive material penetrates into the aperture and seals the aperture and another portion of the electrically conductive material may be deposited at a portion around the aperture.

The step of forming the electrically insulating and/or electrically conductive material may comprise depositing diamond material using chemical vapour deposition (CVD).

The present invention provides in an eighth aspect a method of manufacturing a feedthrough for an implantable medical device, the method comprising the steps of:
- providing a wall portion of a housing of the device;
- forming an aperture through the wall portion;
- forming an electrically conductive material such that the electrically conductive material penetrates though the aperture of the housing portion and is arranged for electrically coupling a component positioned inside the housing with a component that is exterior the housing, the electrically conductive material comprising a nitrogen incorporated diamond material; and forming an electrically insulating material positioned over the electrically conductive material to provide electrical insulation, the electrically insulating material comprising a diamond material;

wherein at least one of the electrically conductive material and the electrically insulating material is at least partially formed by chemical vapour deposition (CVD).

The present invention provides in a ninth aspect a method of manufacturing a feedthrough for an implantable medical device, the method comprising the steps of:

providing a wall portion of a housing of the device, the wall portion being composed of an electrically insulating diamond material;

forming an aperture through the wall portion; and forming an electrically conductive diamond material such that the electrically conductive material penetrates though the aperture of the housing portion and is arranged for electrically coupling a component positioned inside the housing with a component that is exterior the housing, the electrically conductive diamond material being a nitrogen incorporated diamond material;

wherein the electrically conductive diamond material is positioned such that the aperture is sealed and the housing is fluid impermeable in the proximity of the feedthrough.

The invention will be more fully understood from the following description of specific embodiments of the invention. The description is provided with reference to the accompanying drawings.

DETAILED DESCRIPTION OF SPECIFIC EMBODIMENTS

Embodiments of the present invention relate to an electrode and a feedthrough for an implantable medical device. The electrode and the feedthrough comprise electrically conductive and insulating elements. In the embodiment described in the following, both types of components are formed from materials that have substantially the same lattice constants and crystallographic structures. In this example the electrically conductive and insulating elements are formed from a diamond material.

The diamond materials of devices in accordance with embodiment of the present invention are provided in the form of thin films that are formed by thin film growth techniques such as chemical vapour depositions. Electrically insulating diamond layers may for example comprise poly-crystalline diamond material such as hydrogen-incorporated ultra nano-crystalline diamond. Electrically conductive diamond layers may for example comprise nitrogen-incorporated diamond such as nitrogen-incorporated ultra nano-crystalline diamond. It is to be appreciated by a person skilled in the art that the present invention is not limited to these explicit types of diamond material and any diamond material (or diamond like carbon material), having suitable properties may be used.

Additional embodiments of the present invention relate to a medical device comprising an array of the implantable electrodes and electronic components connected to the electrodes. The implantable electrodes and housing portions may form a capsule such that a seal is provided between the electronic components and surrounding tissue when the medical device is implanted in a patient.

Embodiments of the present inventions have applications in the field of retinal prostheses for treatment of particular retinal diseases and for this purpose a retinal prosthesis may be implanted into the retina of a patient. The retinal prosthesis comprises an array of stimulating electrodes that stimulate neurons in an inner cell layer of the retina which is still intact. Thus, at least some degree of sight may be restored.

A person skilled in the art will appreciate that the present invention has many different applications. Further applications relate to the treatment of cardiac diseases, hearing loss or deep brain stimulation.

Figure 1:
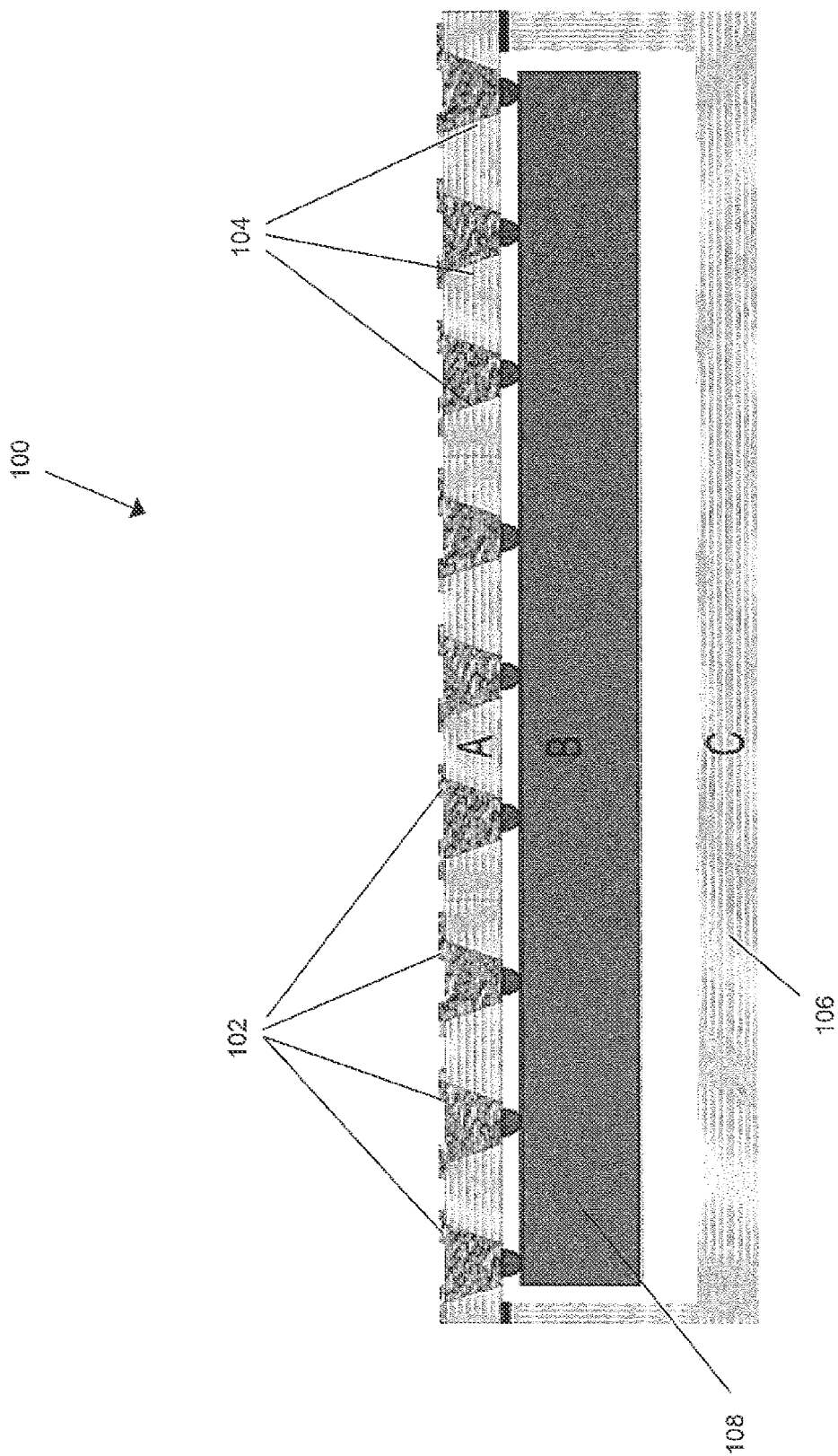
FIG. 1 is a schematic cross-sectional view of a device in accordance with an embodiment of the present invention.

Referring now to FIG. 1, a medical device 100 in accordance with a first specific embodiment of the present invention is described in further detail. The medical device 100 is arranged for implanting into the retina of a patient and for stimulating an inner cell layer of the retina.

Figure 2:
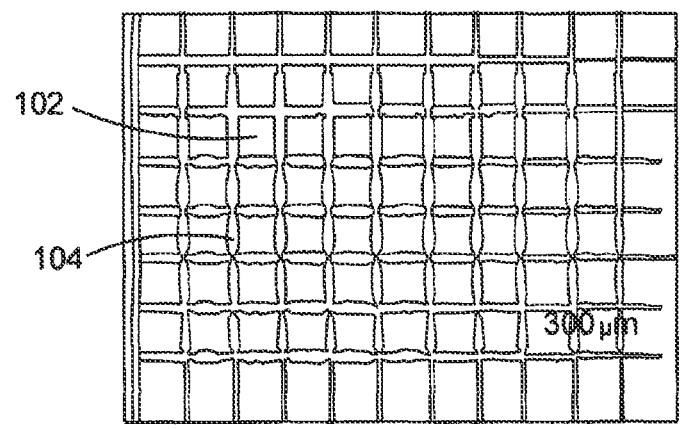
FIG. 2 is a top view of an array of implantable electrodes in accordance with an embodiment of the present invention.

The medical device 100 comprises a plurality of electrically conducting elements 102 and electrically insulating material 104 surrounding portions of the electrically conducting elements 102. The electrically conducting elements 102 form an array. FIG. 2 shows an optical micrograph of the array. An exterior portion of the array is exposed to biological tissue when implanted into a patient. For example, the array may be exposed to nerve tissue in the retina.

The plurality of electrically conducting elements 102 and the electrically insulating elements 104 are composed of diamond material having different electrical properties. In this particular embodiment, the plurality of electrically conducting elements 102 are composed of nitrogen incorporated ultra nano-crystalline diamond material having $sp^2$ and $sp^3$ carbon bonds and the electrically insulating elements 104 are composed of polycrystalline diamond material having primarily sp$^3$ carbon bonds.

Such an implantable array provides a mechanically robust, biocompatible and hermetic seal that is capable of stimulating nerve tissue in the retina.

Figure 3:
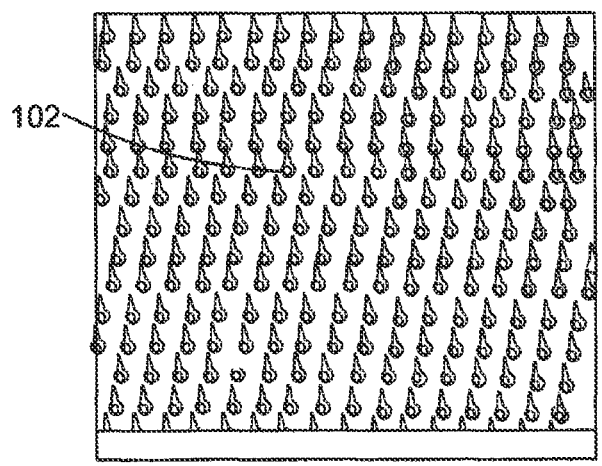
FIG. 3 is a scanning electron microscopy (SEM) image of an array of electrodes in accordance with an embodiment of the present invention.
Figure 4:
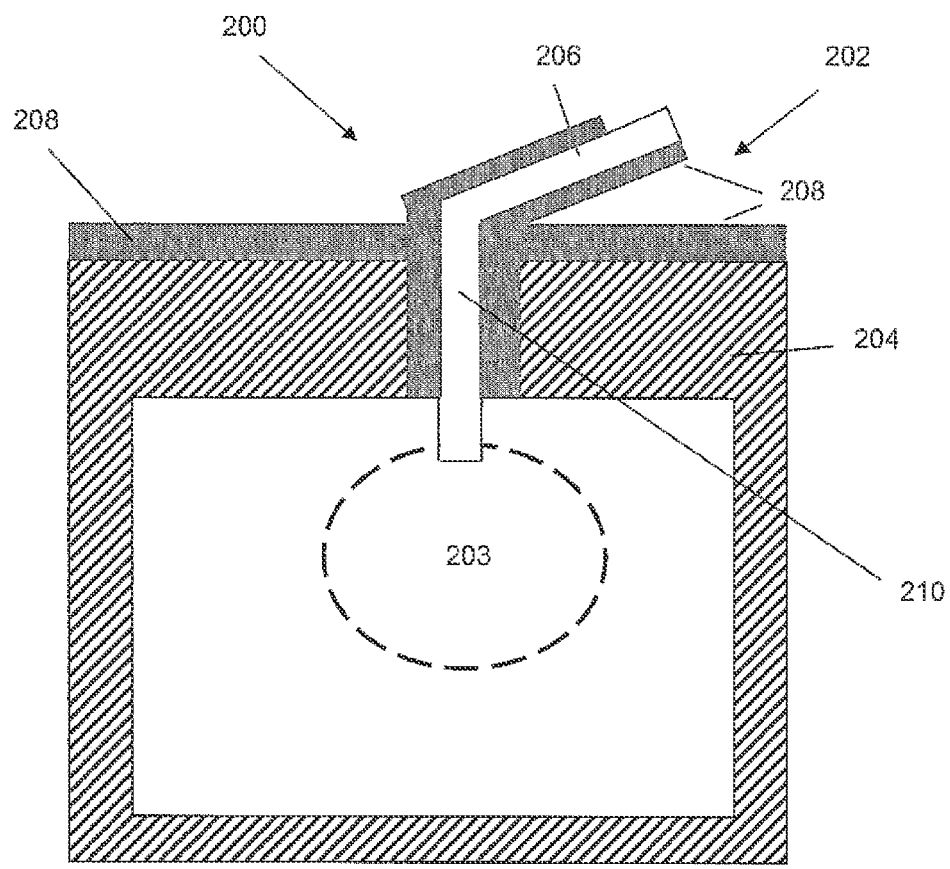
FIG. 4 illustrates a schematic cross-sectional view of a medical device in accordance with an embodiment of the present invention.
Figure 5:
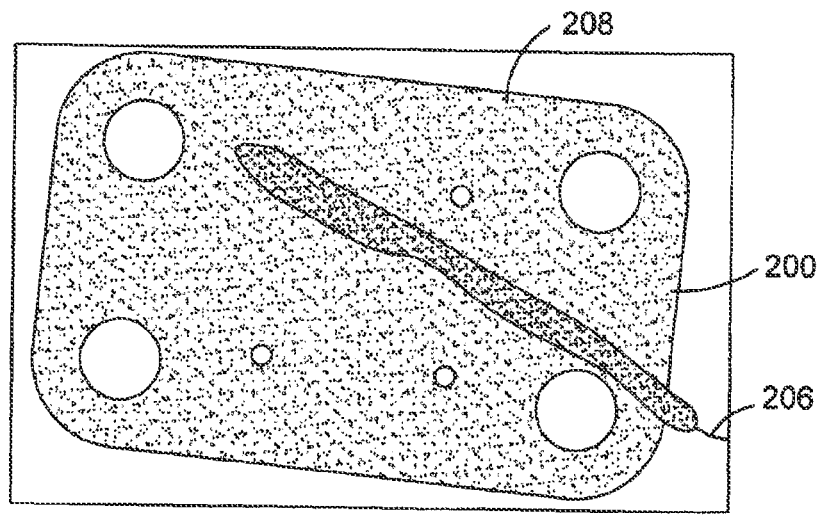
FIGS. 5 and 6 show views of feedthroughs of a medical device in accordance with an embodiment of the present invention.

FIG. 3 shows a SEM micrograph of the implantable array. In this particular embodiment, the electrically conducting elements 102 are provided in the form of pyramids having an approximate diameter of 10 μm and an approximate height of 85 μm. A person skilled in the art will appreciate that an electrically conducting element 102 may have any suitable shape, such as cylindrical or conical.

Referring now back to FIG. 1, the medical device 100 further comprises a housing 106 that is also composed of a diamond material. The housing 106 has an exterior portion that is exposed to biological tissue when implanted into a patient, for example, into a patient's retina. In this particular example, the housing 106 accommodates an electronic chip 108 and may also accommodate other electronic components.

The electronic chip 108 is connected to the electrically conducting elements 102. The electronic chip 108 may be arranged to control stimulating signals or received signals.

In this embodiment, the array of electrodes and the housing 106 form a biocompatible and hermetically sealed capsule comprising the electronic chip 108.

The medical device 100 further comprises a feedthrough (not shown) for electrically connecting the electronic chip 108 to a power supply and further electronic components positioned at a remote location. The feedthrough is provided in the form of the feedthrough as described below with reference to FIGS. 4 to 7.

Referring to now FIGS. 4 to 7, there is a medical device 200 in accordance with an embodiment of the present invention. The medical device 200 has an electrical feedthrough assembly 202. For example the medical device 200 may be a pace maker or a bionic eye device and consequently comprises electronic components 203 that are electrically coupled to exterior components (not shown) via the feedthrough assembly 202. The medical device 200 is arranged for housing the electronic components 203 and is arranged for implantation into the human body.

The feedthrough 202 assembly comprises a wall portion 204 and an aperture 210 extending entirely through the wall portion 204. An electrically conductive wire 206 extends through the aperture 210, which is shown in detail in FIGS. 6 and 7.

Figure 6:
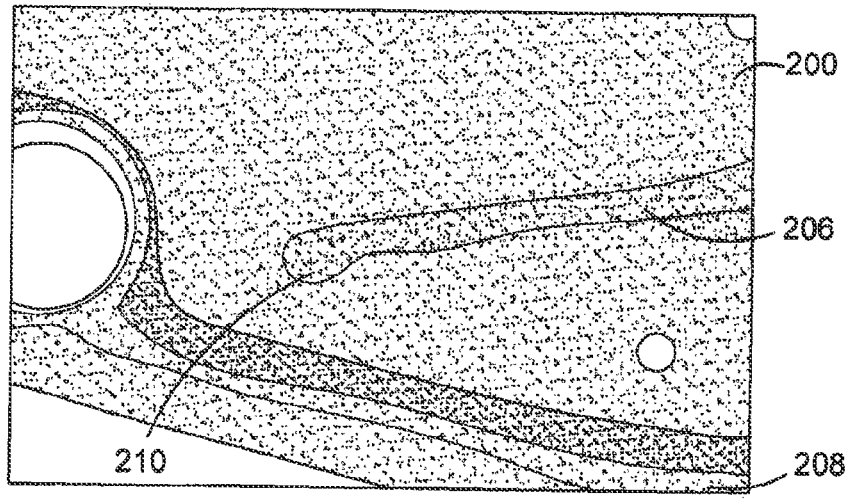
Figure 7:
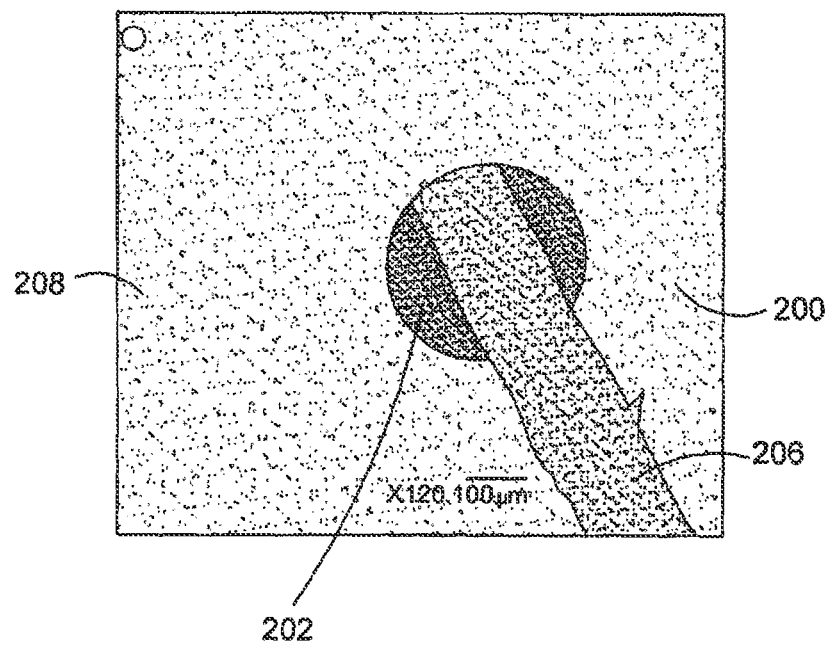
FIG. 7 shows a scanning electron microscope image of the feedthrough shown in FIG. 6.

An exterior surface of the wall portion 204 and a portion of the electrically conductive wire 206 are coated by a layer of an electrically insulating diamond material 208 that penetrates into the aperture 210 and seals the aperture 210 (FIG. 7 shows a view of the feedthrough prior to depositing the electrically insulating diamond material 208 at the aperture 210, but after depositing a diamond material 208 onto a portion of the exterior surface of the wall portion 204). The diamond material 208 encapsulates a portion of the wire 206, which preserves its metallic behaviour and low resistivity. The coverage of the diamond material 208 extends over the exterior surface of the wall portion. The aperture 210 is at least partially filled with the diamond material 208 whereby the wire 206 is irremovably encapsulated by diamond material 208 within the aperture 210 (as shown in FIGS. 6 and 7). The interface between the wire 206 and the diamond material 208 is fluid impermeable.

The diamond material 208 is in this example formed by chemical vapour deposition, which will be described in detail further below. The diamond material 208 comprises a polycrystalline material such as hydrogen-incorporated ultra nano-crystalline diamond. The electrically conductive wire 206 is in this embodiment formed from platinum, but may alternatively also comprise another suitable metallic material, such as gold.

The wire 206 extends at an exterior surface of the wall portion 204 at an acute angle. However, the wire 206 may alternatively also extend in any other orientation and/or may be arranged for coupling to another component at or on the wall portion 204.

Further, it will be appreciated by a person skilled in the art that the embodiment illustrated in FIGS. 4 to 7 may have many variations. For example, the wire 206 may comprise any electrically conductive arrangement, for example a single solid wire, a bundle or single solid wires, or a may be replaced by an electrically conductive track or strip. Further, the device 200 may alternatively comprise a coating of an electrically conductive diamond material that seals the aperture and is covered by an electrically insulating coating, such as a flexible coating, that may or may not comprise a diamond material.

Figure 8:
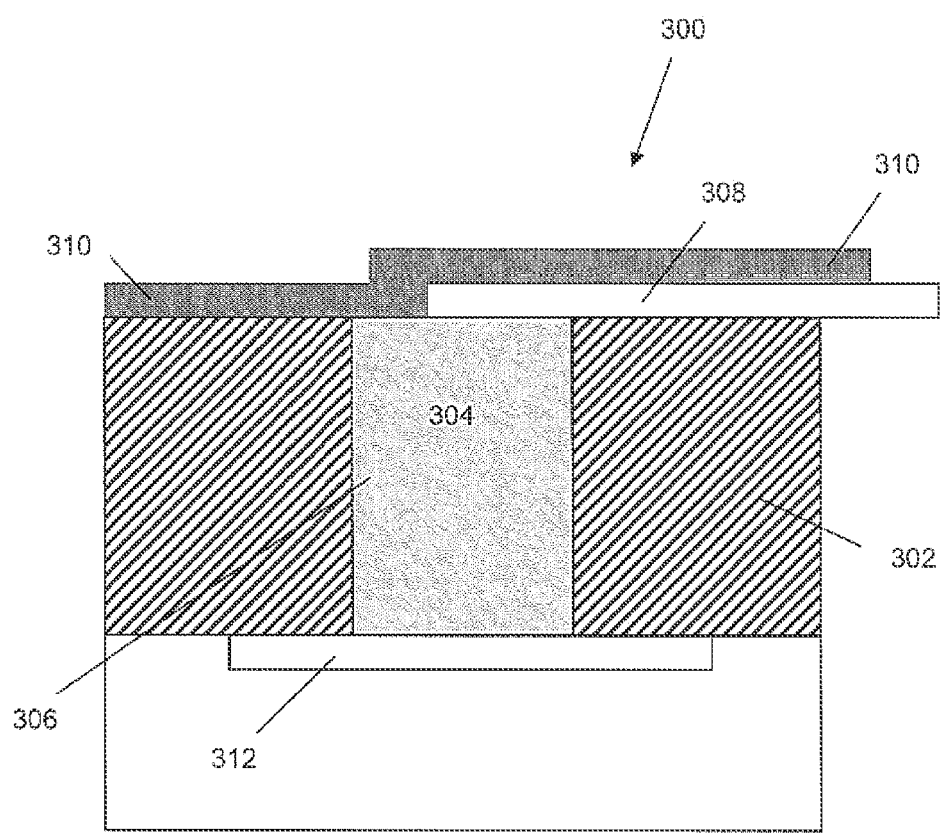
FIG. 8 illustrates a schematic cross-sectional view of a medical device in accordance with an embodiment of the present invention.

FIG. 8 shows a medical device 300 in accordance with a further embodiment of the present invention. Again, the device 300 comprises a wall portion 302 that has an aperture 304. The aperture 304 is filled (sealed) with an electrically conductive material 306, which in this embodiment is an electrically conductive diamond material. The electrically conductive diamond material 306 seals the aperture 304 such that the aperture 304 is fluid and gas impermeable.

In a variation of this embodiment the device may alternatively comprise for example a metallic electrically conductive material that penetrates through the aperture 304. For example, the metallic electrically conductive material may comprise titanium, platinum, iridium or gold. In this case the device 300 comprises a layer of diamond material, such as an electrically insulating diamond material, that seals the aperture 304 around the electrically conductive material.

The electrically conductive diamond material 306 in this example is flush with an exterior surface of the wall portion 302, but may alternatively extend further. For example, if a mask or masking agent (not illustrated) is used to selectively deposit electrically conductive diamond material 306, the electrically conductive diamond material 306 is likely to extend to the vertical dimension of the mask or masking agent.

Figure 9:
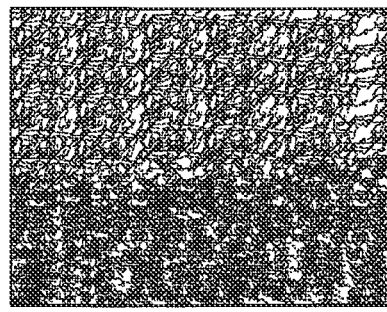
FIG. 9 shows a scanning electron microscope image of a feedthrough according to an embodiment of the present invention and including a wire encapsulated in a non-conductive material.
Figure 10:
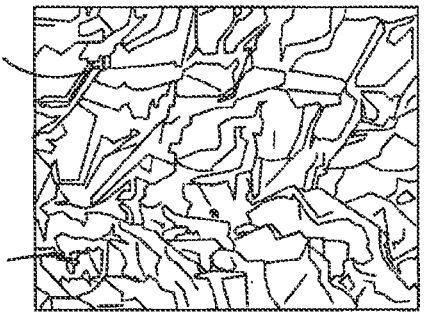
FIG. 10 shows a scanning electron microscope image of the feedthrough shown in FIG. 7 in higher magnification.

An further electrically conductive material 308 (such as a wire or strip of a suitable metallic material) is electrically connected to the electrically conductive diamond material 306 to provide for coupling to external components (not shown). The further electrically conductive material 308 and an exterior surface of the wall portion 302 are coated with electrically non-conductive diamond 310 such that the wall portion 302 is encapsulated by electrically non-conductive diamond 310. The encapsulated electrically conductive materials 316 and 308 preserve their metallic behaviour and low resistivity. FIGS. 9 and 10 show the coatings 308 and 310 and the electrically conductive material in further detail.

Figure 11:
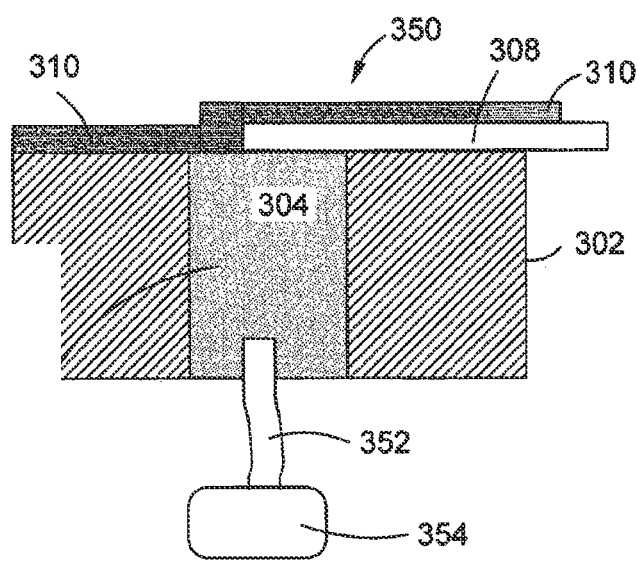
FIG. 11 illustrates a schematic cross-sectional view of a medical device in accordance with another embodiment of the present invention.

FIG. 11 shows a medical device 350 in accordance with a further embodiment of the present invention, which is a variation of the embodiment described above and illustrated in FIGS. 8 to 10 and the same reference numerals are used to ease illustration. FIG. 11 illustrates an alternative for electrically coupling the electronic component 312 to the electrically conductive diamond material 306. One end of an electrically conductive wire 352 is engaged within the aperture 304 and the other end of the electrically conductive wire 352 is electrically connected to the electronic component 354. In this embodiment the electrically conductive wire 352 may for example be formed from platinum or another suitable metallic material and does not fully extend through into the electrically conductive material 306.

Figure 12:
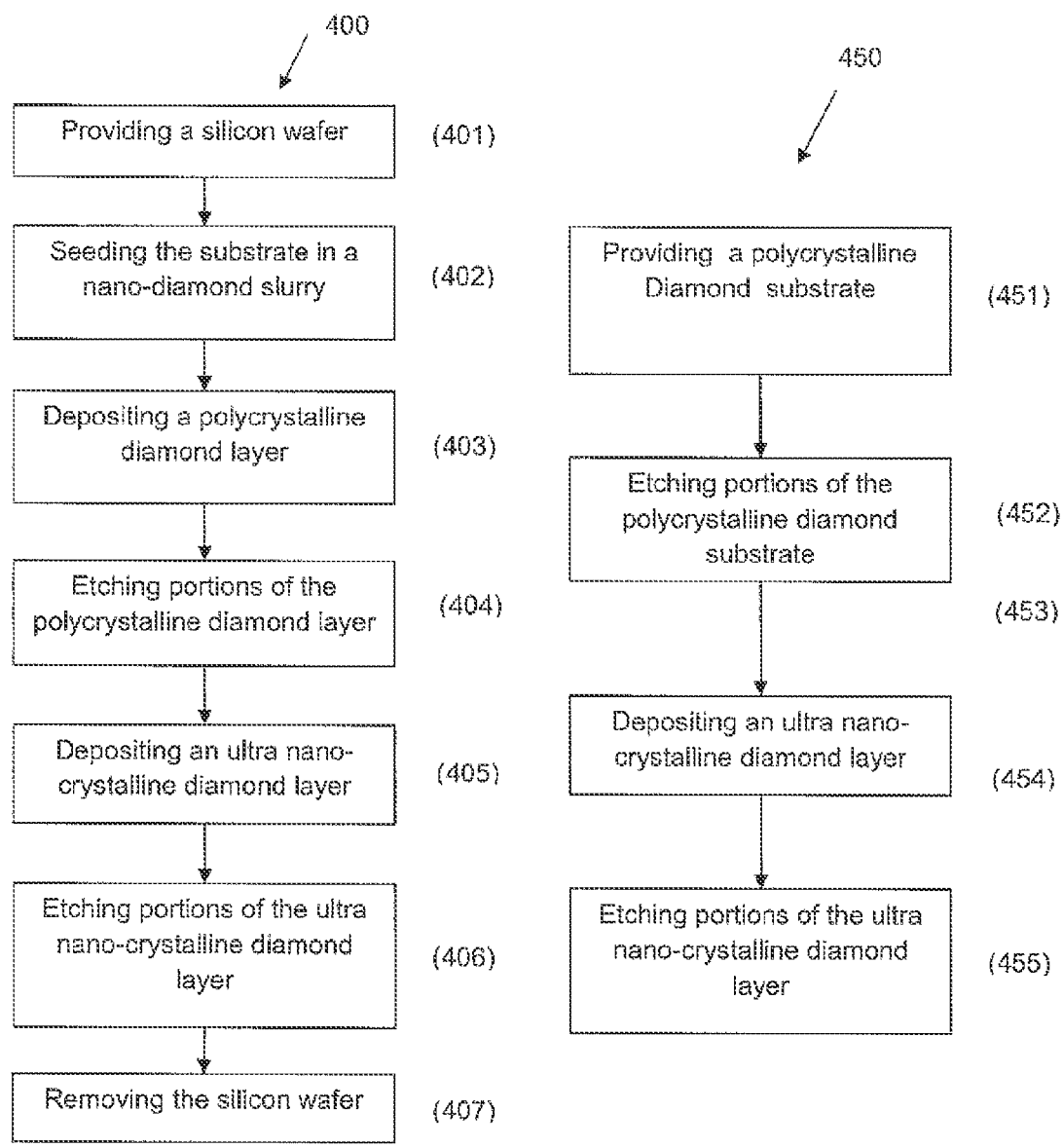
FIGS. 12-19 are flow charts illustrating methods of in accordance with embodiments of the present invention.
Figure 13:
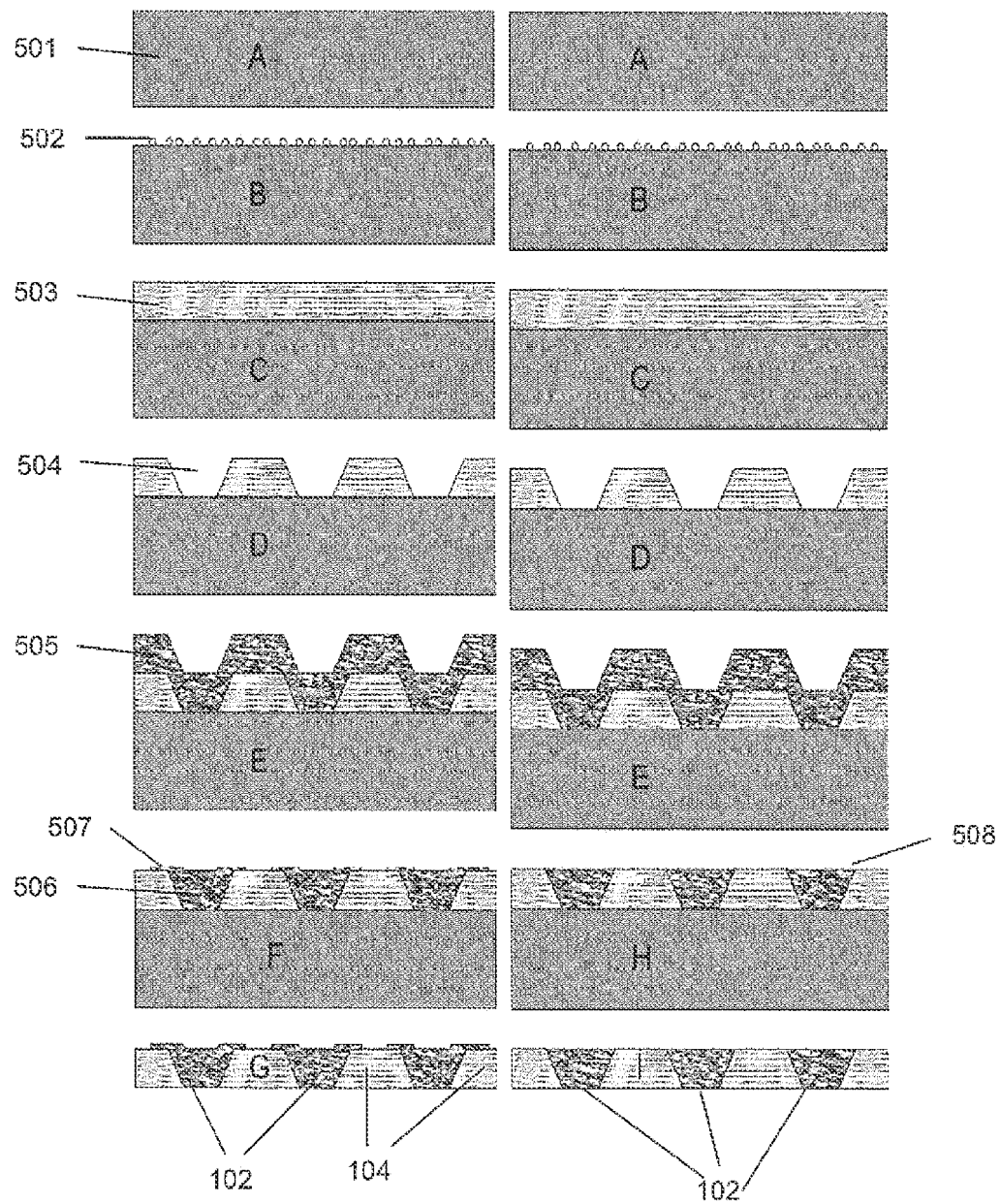
Figure 14:
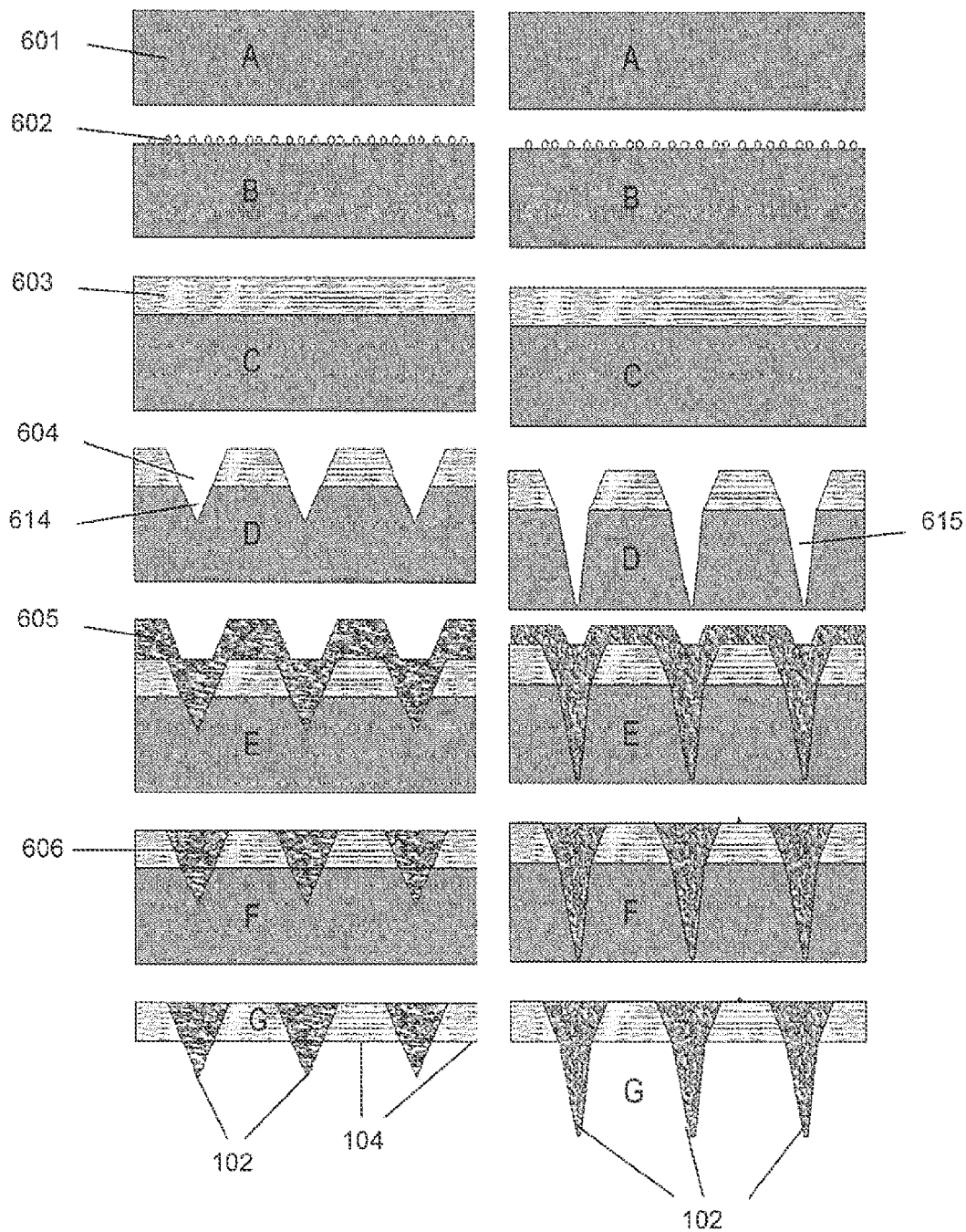
Figure 15:
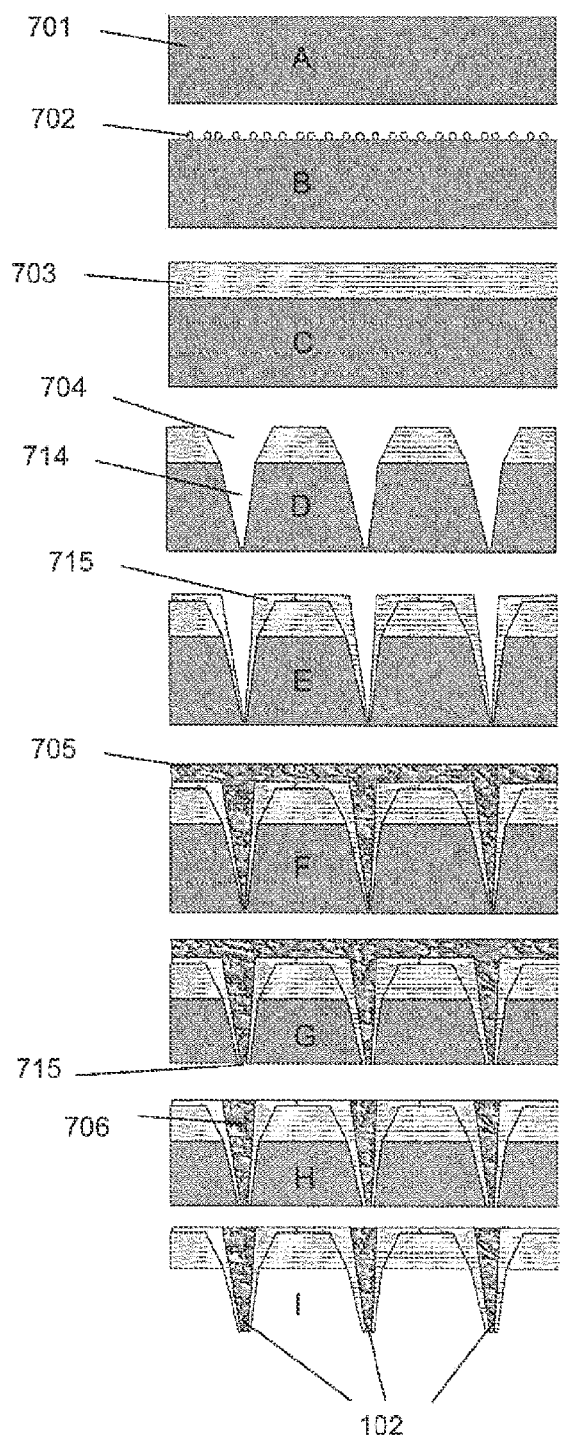

FIG. 12 (*a*) shows a flow diagram of a method 400 in accordance with an embodiment of the present invention and FIGS. 13, 14 and 15 illustrate steps of the method 400 in further detail.

A chemical vapour deposition system, such as a microwave plasma chemical vapour deposition system, is used to manufacture components of the implantable feedthrough as described above with reference to FIGS. 1 to 3 or the implantable electrode as described above with reference to FIGS. 4 to 11. However, a person skilled in the art will appreciate that other systems to manufacture an implantable electrode are envisaged.

Initially fabrication of the implantable electrode is described. In a first step 401 of method 400, a silicon substrate 501, 601, 701 is provided. In this particular example, the substrate 501, 601, 701 is a single side polished P-type silicon wafer of 300-500 μm. A person skilled in the art will appreciate that other materials are envisaged, such as glass or quartz.

A subsequent seeding step 402 is performed by immersing the substrate 501, 601, 701 in a nano-diamond slurry in ultrasonic bath to form a seeding layer (502, 602, 702). In this particular example, the substrate 501, 601, 701 is placed in a solution of methanol comprising the 4-6 nm detonated diamond powder at a concentration of 4 g/litre. The substrate 501, 601, 701 is held upright with a pair of tweezers with the solution placed in an ultrasonic bath to ensure even diamond dispersion. Subsequently, the substrate 501, 601, 701 is dried by dry nitrogen gas. A person skilled in the art will appreciate that the seeding step 402 may be performed by any other suitable method, such as spraying, spin-coating and bios enhanced nucleation.

In a third step 403, a first gas mixture of methane ($CH_4$, 2%) and hydrogen ($H_2$, 98%) is used to form the electrically insulating material 104. In this particular example, a polycrystalline diamond layer 503, 603, 703 of approximately 10-100 μm is grown using a a $H_2/CH_4$ (750 sccm/15 sccm) gas mixture at a pressure of 80 Torr and a temperature of approximately 900-1100° C. A person skilled in the art will appreciate that any suitable gas mixture may be used to form the electrically insulating material 104.

The seeded substrate is placed within a microwave plasma chamber of a microwave plasma CVD system (2.45 GHz/6 kW continuous wave, microwave power: 1-3 kW). The seeded substrate is then exposed to the hydrogen-methane plasma for a period between 10 and 100 hours. The deposition rate in this particular example is 1-2 microns per hours. A layer of approximately 50-100 μm of the polycrystalline diamond layer 503, 603, 703 is required for a mechanically stable and relatively robust 10×10 mm diamond slap. However, a person skilled in the art will appreciate that an optimal thickness of the polycrystalline diamond layer 503, 603, 703 depends on the size of the desired diamond slap.

In a further step (404), portions of the polycrystalline diamond layer 503, 603, 703 are removed using a laser radiation or etching such as reactive ion etching or wet etching. Resulting voids 504, 604, 704 provide a basis for forming the electrically conducting elements 102. Additionally, also portions of the silicon wafer 614, 615, 714 may be removed using the laser radiation or etching. In this particular example, the size of the portions 614, 615, 714 that are removed from the silicon wafer determines the form and height of the electrically conducting elements 102. The electrically conducting elements 102 may, for example, be formed in a shape of a pyramid, a cylinder or a cone.

Optionally, a further layer 715 of polycrystalline diamond material is grown as shown in FIG. 15.

Step 405 is a further seeding step for forming a layer of electrically conducting diamond material. Using a second gas mixture of Argon (Ar, 70-80%), methane ($CH_4$, 1-5%) and Nitrogen ($N_2$, 5-20%), a layer of the electrically conducting diamond (505, 605, 705) material is formed. In this particular example, a gas mixture Ar/N2/CH4 (79 sccm/20 sccm/1sccm) is used at a pressure of 80-120 Torr and a temperature of 900° C. The growth rate in this example is approximately 0.75 μm/hour. In this particular example, a layer of approximately 10-100 μm of nitrogen incorporated ultra nano-crystalline diamond (505, 605) is grown using the abovementioned gas mixture.

If the sample comprises the further insulating layer of polycrystalline diamond material 715, a further step of etching may be required to remove portions of the further insulating layer 715 on tips of the conducting diamond material 705, as exemplarily shown in FIG. 15. In this step, portions of the substrate 701 may also be removed.

In a further step 406, portions of the ultra nano-crystalline diamond layer are removed by etching or laser radiation such that a plurality of isolated electrically conducting elements 506, 606, 706 is provided within the polycrystalline diamond layer. Portions of the ultra nano-crystalline diamond layer are removed such that projections 507 remain. Alternatively, portions of the ultra nano-crystalline diamond layer may be removed such that a flat surface 508 is provided.

In a further step 407, the substrate is removed by etching such that an array of implantable electrodes is provided. In this example, the substrate is removed by placing the sample in a nitric acid/hydrofluoric acid/acetic acid (10/1/1)v/v mixture.

In this particular example, three electrically conducting elements 102 form one row of the array. A person skilled in the art will appreciate that any suitable size and any suitable density of the electrically conducting elements 102 of the array are envisaged.

Figure 16:
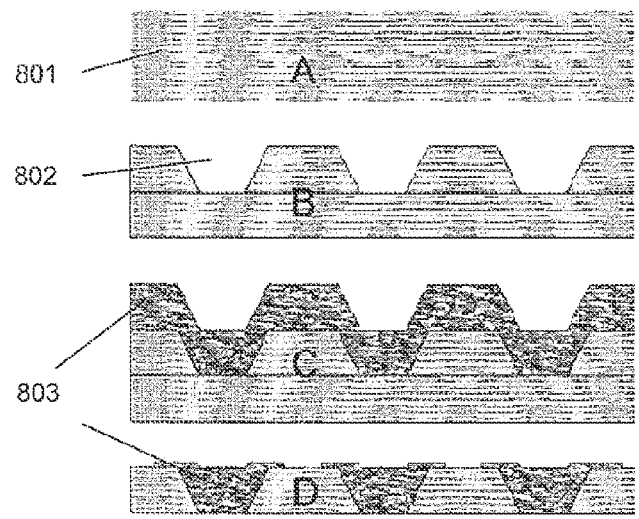
Figure 16:
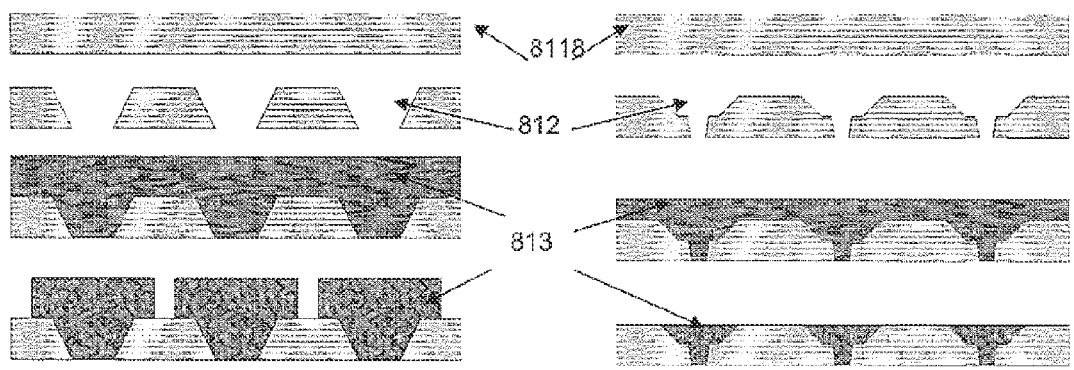

Referring now to FIG. 16 (*a*), another embodiment of the method is illustrated. In this particular embodiment, plates 801 are provided and which comprise a polycrystalline or single crystalline diamond material that is positioned on a substrate, such as a silicon substrate. In a next step, a laser beam is used to remove portions 802 of the polycrystalline or single crystalline diamond material. In this particular example, a diode pumped solid state laser with a wavelength of 532 nm is used. A pre-defined pattern is used, to remove the portions 802.

The remaining steps form conductive diamond material 803 and are performed in accordance with the method 400 and illustrated with reference to FIG. 12 (*a*).

Referring now to FIGS. 12 (*b*), 16 (*b*) and 16 (*c*), another fabrication method in accordance with an embodiment of the present invention is now described. The illustration of FIGS. 16 (*b*) and 16 (*c*) is related to that of FIG. 16 (*a*). The method 450 includes the initial step 451 of providing a polycrystalline electrically insulating diamond substrate 811. In this embodiment, the diamond substrate 811 is provided without a supporting silicon substrate. The method 450 further includes step 453 etching portions 812 of the polycrystalline diamond layer 811 and depositing an ultra nano-crystalline and electrically conductive diamond layer 813 (step 454). Further, the method 450 includes the step of etching portions of the ultra nano-crystalline diamond layer 813 to form the desired structure.

Figure 17:
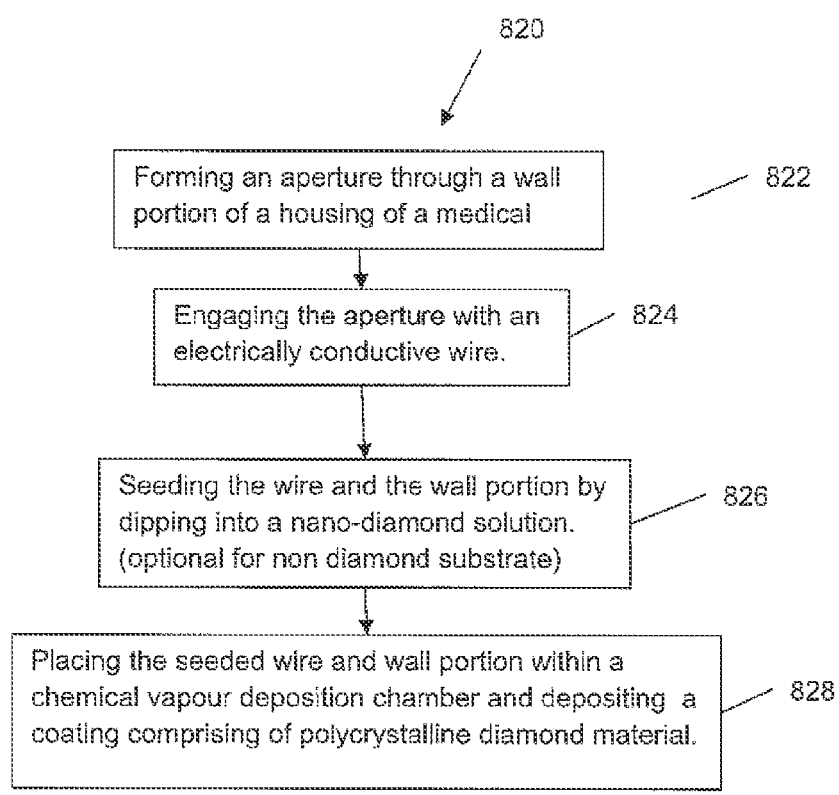

The following will describe a method of fabricating a feedthrough in accordance with embodiments of the present invention in further detail and which is related to the above-described methods 400 and 450 of fabricating the implantable electrode. FIG. 17 illustrates a method 820, which comprises step 822 of forming an aperture through a wall portion of a housing of a medical device. Step 824 engages the aperture with at least one electrically conductive wire that is manually positioned. Step 826 seeds the wire and the wall portion by physically dipping both into a nano-diamond solution. The nano-diamond solution comprises diamond nano-crystals having a size of 1-1000 nm and that are suspended within a solvent such as a methanol solution. In this embodiment, the dipping of the wire and the wall portion in the suspension is performed under sonication to ensure an equal dispersion upon the wall portion and the wire.

The seeded wire and wall portion are then placed within a chemical vapour deposition chamber to deposit coating comprising of polycrystalline electrically insulating diamond material (step 828). The chemical vapour deposition chamber has an energy source, which may be provided in the form of a microwave, hot filament or arc discharge source. The chemical vapour deposition is operated under a flow of methane and hydrogen and at an operating pressure of 60-120 Torr. The ratio of methane and hydrogen is controlled dependant on the deposition coating required.

The diamond material is grown at reduced pressures and temperatures between 900 and 1200° C. The inclusion of hydrogen gas prevents the formation of graphite. As the diamond nucleates and grows and by altering the gas chemistry one can grow diamond materials with different mechanical and electrical structures. In the current embodiment, a methane/hydrogen ratio of 5/95 was used to deposit polycrystalline diamond.

After chemical vapour deposition of the diamond material, the wall portion with the wire is removed from the chamber. The wall portion and exposed portions of the wire are coated in poly-crystalline diamond, which is rigid and cannot easily be moved relative to the substrate. The aperture defined within the substrate is at least partially encapsulated by diamond material and the wire is encapsulated within the aperture. The diamond material seals the aperture such that the contact regions between the substrate and the diamond material are fluid and gas impermeable.

The wire may also be masked before the wire and wall portion are placed within a chemical vapour deposition chamber, such that an exposed end-portion of the wire is not coated by the diamond material.

Figure 18:
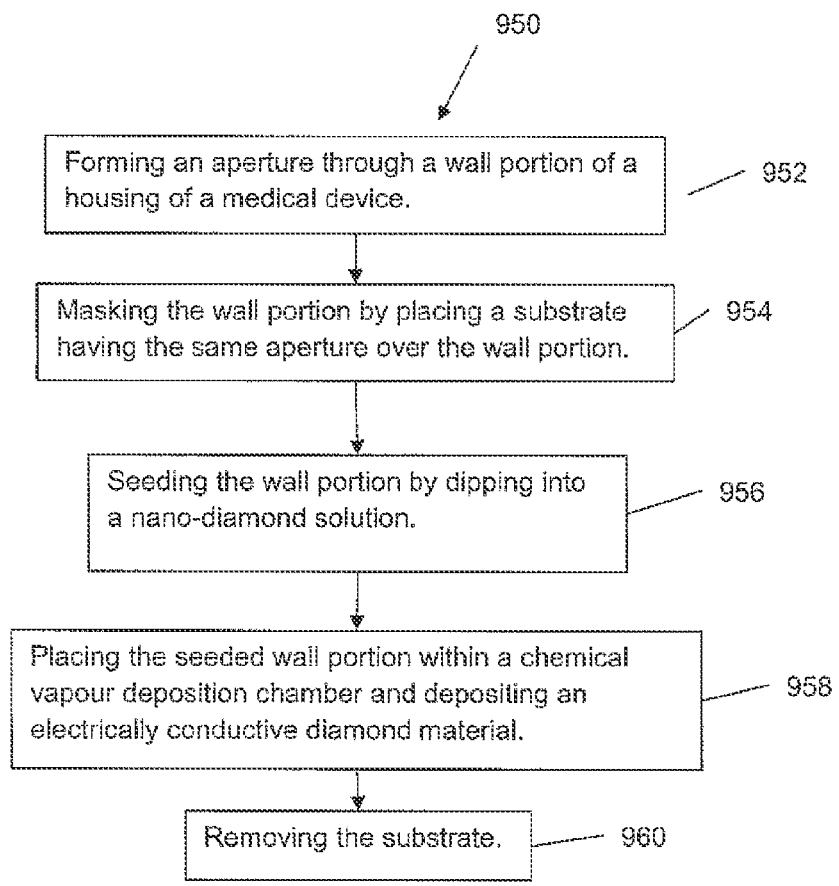

In another variation the feedthrough may be fabricated using method 900 which is illustrated in FIG. 18. Method 950 comprises the initial step 952 of forming an aperture in an electrically non-conductive wall portion of the device. The wall portion is masked by placing a substrate having the same aperture over the wall portion (step 954). The wall portion and the substrate are seeded by physically dipping both in a nano-diamond solution comprising 4-6 nm diamond nano-crystals suspended within methanol solution (step 956).

The seeded wall portion and substrate are placed within a chemical vapour deposition chamber (step 958). The chemical vapour deposition is operated under a flow of methane, nitrogen and argon to deposit an electrically conductive diamond material. In this embodiment, the electrically conductive diamond is nitrogen-incorporated ultra-nanocrystalline diamond including 1-2% methane, 5-250 nitrogen and 74-94% argon. A sample stage on which the wall portion and the substrate are positions stage is heated to 800-900° C. during chemical vapour deposition.

After chemical vapour deposition the substrate is removed from alignment with the wall portion (step 960). The aperture of the wall portion is filled with electrically conductive diamond material and the electrically conductive diamond irremovably seals the aperture. The electrically conductive diamond seals the aperture such that the contact regions between the substrate and the diamond are fluid and gas impermeable. Electrically conductive diamond layers may be formed in the described manner to contact the electrically conductive material that fills the aperture. Again, electrically a layer of electrically insulating material is finally deposited to establish electrical insulation of the electrically conductive material.

Figure 19:
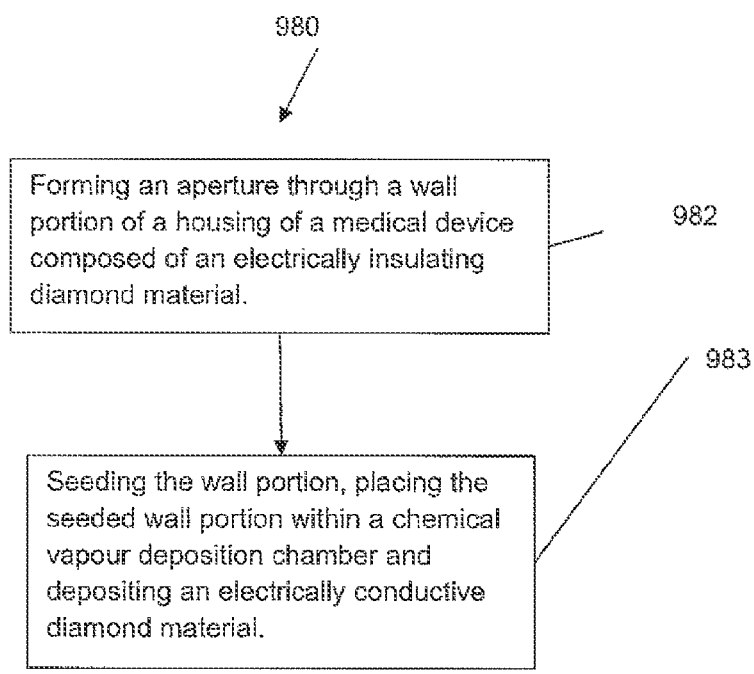

FIG. 19 illustrates a further variation of a method of forming an implantable feedthrough. Method 980 comprises the initial step 982 of forming an aperture through a wall portion of a housing of a medical device that is composed of an insulating diamond material. Further, the method 980 comprises step 983 of seeding the wall portion, placing the seeded wall portion within a chemical vapour deposition chamber and depositing an electrically conductive diamond material to fill the aperture and form the feedthrough.

Although the invention has been described with reference to particular examples, it will be appreciated by those skilled in the art that the invention may be embodied in many other forms.

The invention claimed is:

1. An electrode for an implantable medical device, the electrode comprising:
   a plurality of electrically conductive elements comprising a diamond material, the diamond material being a nitrogen incorporated diamond material comprising $sp^2$ and $sp^3$ carbon bonds, the diamond material being, in use, arranged for stimulating neurons; and
   at least one electrically insulating element covering at least a portion of each electrically conductive element and comprising a diamond material.

2. The electrode of claim 1 wherein the electrode is exclusively formed from a diamond material.

3. The electrode of claim 1 wherein the electrode comprises exclusively a diamond material and a metallic material.

4. The electrode of claim 1 wherein the diamond material of the at least one electrically insulating element comprises a dopant or incorporated material that influences an electrical property of the material.

5. The electrode of claim 1 wherein each electrically conductive element is in direct contact with and the at least one electrically insulating element and an interface between the electrically conductive elements and the at least one electrically insulating element is hermetically sealed.

6. The electrode of claim 1 wherein the nitrogen incorporated diamond material of the at least one electrically conductive element is a nitrogen incorporated nano-crystalline diamond material.

7. An electrode for an implantable medical device, the electrode comprising:
   a plurality of electrically conductive elements formed from a first material that comprises an electrically conductive nitrogen incorporated diamond material comprising $sp^2$ and $sp^3$ carbon bonds, the diamond material being, in use, arranged for stimulating neurons; and
   at least one electrically insulating element formed from a second material and covering at least a portion of each electrically conductive element;

wherein the first and second materials have substantially the same crystallographic structures and lattice constants.

8. A medical device comprising the electrode in accordance with claim 1, the medical device comprising:
a housing portion that defines an interior region; and
electronic components positioned in the interior region of the housing portion.

9. The medical device of claim 8 wherein the electrode comprises an array of the electrically conducive elements and forms a lid of the housing portion.

10. A method of manufacturing an electrode for an implantable medical device, the method comprising the steps of:
forming a plurality of electrically conductive elements comprising a diamond material, the diamond material being a nitrogen incorporated diamond material comprising $sp^2$ and $sp^3$ carbon bonds, the diamond material being, in use, arranged for stimulating neurons; and
forming a least one electrically insulating element that covers at least portions of the electrically conductive elements and comprises a diamond material in a manner such that the diamond material of the electrically conductive elements and the diamond material of the at least one electrically insulating element are in direct contact and an interface between the first and second materials is hermetically sealed.

11. A method of manufacturing an electrode for an implantable medical device, the method comprising the steps of:
forming a plurality of electrically conductive elements comprising an electrically conductive nitrogen incorporated diamond material comprising $sp^2$ and $sp^3$ carbon bonds, the diamond material being, in use, arranged for stimulating neurons; and
forming a least one electrically insulating element that covers at least portions of the electrically conductive elements and comprises a second material in a manner such that the electrically conductive nitrogen incorporated diamond material and the second material are in direct contact and an interface between the materials is hermetically sealed;
wherein the materials have substantially the same crystallographic structure and lattice constant.

12. The method of claim 11 wherein the second material is a diamond material.

13. An implantable medical device having an electrical feedthrough, the device comprising:
a housing portion having an exterior surface and an aperture;
an electrically conductive material penetrating though the aperture of the housing portion and being arranged for electrically coupling a component positioned inside the housing with a component that is exterior the housing, the electrically conductive material comprising a diamond material, the diamond material being a nitrogen incorporated diamond material comprising $sp^2$ and $sp^3$ carbon bonds; and
an electrically insulating material positioned over the electrically conductive material to provide electrical insulation, the electrically insulating material comprising a diamond material;
wherein the electrically conductive and the electrically insulating materials are arranged such that the aperture is sealed and the housing is fluid impermeable in the proximity of the feedthrough.

14. The device of claim 13 wherein the aperture is sealed around the electrically conductive material using a single material component.

15. The device of claim 13 wherein the electrically insulating material comprises a first portion that has penetrated into the aperture and provides a seal between the electrically conductive material and the housing portion and a second portion that coats a portion of the housing portion around the aperture.

16. The device of claim 15 wherein the first and second portions of the electrically insulating material comprise the diamond material and are integrally formed and form one part that is rigidly coupled to the housing portion and the electrically conductive material.

17. A method of manufacturing a feedthrough for an implantable medical device, the method comprising the steps of:
providing a wall portion of a housing of the device;
forming an aperture through the wall portion;
forming an electrically conductive material such that the electrically conductive material penetrates though the aperture of the housing portion and is arranged for electrically coupling a component positioned inside the housing with a component that is exterior the housing, the electrically conductive material comprising a nitrogen incorporated diamond material comprising $sp^2$ and $sp^3$ carbon bonds; and
forming an electrically insulating material positioned over the electrically conductive material to provide electrical insulation, the electrically insulating material comprising a diamond material;
wherein at least one of the electrically conductive and the electrically insulating material is positioned such that the aperture is sealed and the housing is fluid impermeable in the proximity of the feedthrough.

18. The method of claim 17 wherein the step of forming the electrically insulating and the electrically conductive materials comprises depositing diamond material using chemical vapour deposition (CVD).

19. A method of manufacturing a feedthrough for an implantable medical device, the method comprising the steps of:
providing a wall portion of a housing of the device;
forming an aperture through the wall portion; forming an electrically conductive material such that the electrically conductive material penetrates though the aperture of the housing portion and is arranged for electrically coupling a component positioned inside the housing with a component that is exterior the housing, the electrically conductive material comprising a nitrogen incorporated diamond material comprising $sp^2$ and $sp^3$ carbon bonds; and
forming an electrically insulating material positioned over the electrically conductive material to provide electrical insulation, the electrically insulating material comprising a diamond material;
wherein at least one of the electrically conductive material and the electrically insulating material is at least partially formed by chemical vapour deposition (CVD).

20. A method of manufacturing a feedthrough for an implantable medical device, the method comprising the steps of:
providing a wall portion of a housing of the device, the wall portion being composed of an electrically insulating diamond material;
forming an aperture through the wall portion; and forming an electrically conductive diamond material such that the electrically conductive material penetrates though the aperture of the housing portion and is arranged for electrically coupling a component positioned inside the housing with a component that is exterior the housing, the electrically conductive diamond material being a nitrogen incorporated diamond material comprising $sp^2$ and $sp^3$ carbon bonds;

wherein the electrically conductive diamond material is positioned such that the aperture is sealed and the housing is fluid impermeable in the proximity of the feedthrough.

\* \* \* \* \*